United States Patent

Panster et al.

[11] 4,410,669
[45] Oct. 18, 1983

[54] POLYMERIC AMMONIUM COMPOUNDS WITH A SILICA-TYPE BACKBONE, PROCESSES FOR THEIR PREPARATION AND USE

[75] Inventors: Peter Panster, Rodenbach; Peter Kleinschmit, Hanau, both of Fed. Rep. of Germany

[73] Assignee: Degussa Aktiengesellschaft, Frankfurt, Fed. Rep. of Germany

[21] Appl. No.: 376,881

[22] Filed: May 10, 1982

[30] Foreign Application Priority Data

May 21, 1981 [DE] Fed. Rep. of Germany ....... 3120195

[51] Int. Cl.$^3$ .......................................... C08F 283/00
[52] U.S. Cl. .................................... 525/474; 210/684; 521/30; 528/481
[58] Field of Search .......................... 525/474; 521/30; 528/481; 210/684

[56] References Cited

U.S. PATENT DOCUMENTS 2,972,598 2/1961 Morehouse ......................... 525/474
3,862,059 1/1975 Greco et al. ......................... 521/30
4,255,276 3/1981 Fahn et al. ......................... 210/684

Primary Examiner—Melvyn I. Marquis
Attorney, Agent, or Firm—Beveridge, DeGrandi & Kline

[57] ABSTRACT

Polymeric ammonium compounds are disclosed which have a silica-type backbone, comprised of units having the formula:

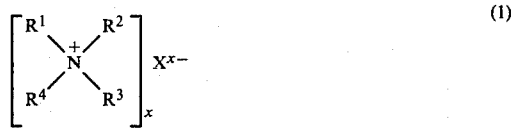

in which $R^1$ and $R^2$ represent a group

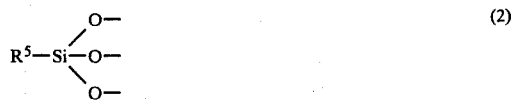

in which $R^5$ is an alkylene grouping and the free valencies of the oxygen atoms are saturated by silicon atoms of further groups (2), if appropriate with incroporation of crosslinking agents, $R^3$ and $R^4$ have the meaning of $R^1$ and $R^2$ or represent hydrogen, an alkyl group, cycloalkyl group or the benzyl group, X represents a 1- to 3-valent anion of a protonic acid which forms stable salts with amine bases and x can be a number from 1 to 3. Also disclosed are processes for preparing the polymeric ammonium compounds and to the use of these materials as ion exchange materials.

59 Claims, No Drawings

POLYMERIC AMMONIUM COMPOUNDS WITH A SILICA-TYPE BACKBONE, PROCESSES FOR THEIR PREPARATION AND USE

The invention relates to new polymeric ammonium compounds with a silica-type backbone which have a series of advantages over known organically based polymeric ammonium compounds. Processes for preparing and using these new products are also described.

Ammonium compounds bonded to organic polymers are widely used in chemical synthesis, application and industry, in particular as ion exchange materials, catalyst supports, active compound supports in general and heterogeneous phase-transfer catalysts. Examples of these uses are described, for example in review form in Ullmanns Enzyklopädie der technischen Chemie (Ullmann's Encyclopedia of Industrial Chemistry), 4th Edition, Volume 13, page 279 or Chem.-Ing. Tech. 51, 7, 728 (1979), in German OLS Nos. 1,800,371 and 1,800,389 or in J.A.C.S., 97, 5956 (1975).

When using these compounds, the organic polymer matrix in some cases substantially satisfies the demands placed on it in respect of thermal and mechanical stability, inertness toward chemical attack, accessibility to the functional groups and solubility in the solvent used. However, in numerous other cases problems arise due to the fact that the organic matrix skeleton, which does not have a fixed structure, is stable only up to at most about 130° C., is chemically degraded too rapidly, swells excessively in the reaction medium used, is incipiently dissolved and becomes tacky, or the functional groups are not accessible at all, or a relatively rapid elimination of amine takes place since the N atom is bonded to the polymer matrix only via one hydrocarbon grouping. The known polymers of this type have a further serious disadvantage inasmuch as increasingly scarcer petroleum and coal reserves fail to guarantee absolute long-term availability of suitable raw materials, so that to change these systems over to an inorganic matrix prepared from raw materials of almost unlimited availability would be generally desirable. Inorganic polymer systems, such as, for example, pyrogenic or precipitated silica, alumina, titania and the like, additionally have other advantages, such as fixed rigid structure, non-swellability high resistance to heat and aging, insolubility and ready accessibility to functional groups which may be present, since the latter are usually situated at the surface. It is understandable that these considerations have already led to attempts, described in German OLS No. 2,433,409, to fix suitable groupings on inorganic support materials, such as silica gel or alumina, and obtain polymer systems which contain ammonium groups and have good application properties, but in view of the only very limited extent to which functional groups can be introduced, these attempts employed only very slight success since corresponding ion exchange materials have a capacity of only 0.5 mEq/g.

Recently it became possible, for the first time, to synthesize polymeric amines which have a silicon-type backbone and which, in contrast to amines bonded to an inorganic support, are distinguished by the high degree to which functional groups can be introduced; i.e. by an almost optimum content of nitrogen per unit weight, and which, as regards the particle size distribution, can be optimized, so that polymeric amines are available which have a series of advantages over the known organically or inorganically based types in respect of matters discussed above. It has now been possible to find that reacting these new polymeric amines with protonic acids or an organic halide produces new polymeric ammonium compounds which possess the properties required, such as fixed structure, non-swellability, a high heat resistance of over 200° C., insolubility, ready accessibility to the functional groups and high inertness toward elimination of amine and which can be used for the applications mentioned at the outset.

The fact which is particularly surprising in the case of these polymeric ammonium compounds according to the invention is that quaternizing the corresponding polymeric amines produces, depending on the number of Si atoms per N atom in the latter, different products in such a way that in the case of 2 Si atoms per quaternized N atom, products are obtained which are soluble in hot water and in the case of 3 or 4 Si atoms per N atom products are obtained which are totally insoluble in water. The latter products are of course therefore to be considered as preferable.

The preparation of polymeric ammonium compounds is also possible by means of a second process according to the invention. This second route initially involves the primary reaction of suitable substituted monomeric amines with an organic halide or a protonic acid and only then the hydrolysis and condensation of the quaternary salts formed. Further representatives of the polymeric ammonium compounds according to the invention can be prepared by a third route, namely by simple ion exchange on polymeric compounds obtained by one of the two above-mentioned variants.

All these processes produce polymeric ammonium compounds which, as regards their physical properties, resemble special silica gels or modified silica gels, have the analytical composition expected from the complete elimination of the hydrolyzable groups present on the monomeric precursors and the chemical behavior of which confirms that conversion into the polymer form has not altered the structure and functionality of the ammonium units. The processes mentioned will be explained in more detail below. The matrix of these polymeric ammonium compounds can be, so to speak, tailored to requirements since it is possible to introduce hetero-atoms such as aluminum or titanium into the matrix or generally to reduce the ammonium group density or to influence the ion selectivity by the degree of crosslinking in the case of use as ion exchange material.

Any polymeric ammonium compound according to the invention is comprised of units of the general formula (1)

in which $R^1$ and $R^2$ represent a group of the general formula (2)

in which $R^5$ in turn represents an alkylene group having 1 to 10 C atoms, a cycloalkylene group having 5 to 8 C atoms,

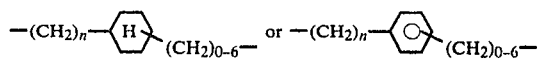

in which n can be a number from 1 to 6 and indicates the number of nitrogen-terminated methylene groups, and $R^1$ and $R^2$ can be identical or different, and the free valencies of the oxygen atoms are saturated either by silicon atoms of further groups of the formula (2) and/or by crosslinking bridge members

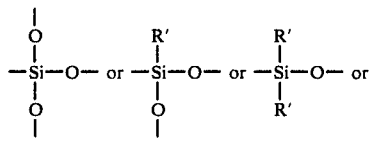

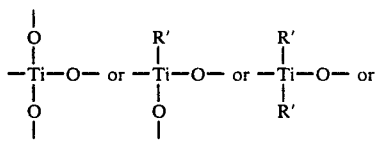

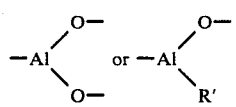

in which R' is a methyl or ethyl group and the ratio of the silicon atoms in (2) to the bridge atoms silicon, titanium and aluminum can be 1:0 to 1:10, $R^3$ and $R^4$ can have the same scope of meaning as $R^1$ and $R^2$ or represent hydrogen, a linear or branched alkyl group containing 1 to 20 C atoms, a cycloalkyl group containing 5 to 8 C atoms or the benzyl group and $R^3$ and $R^4$ can be identical or different and be identical or different to $R^1$ and/or $R^2$, X represents an inorganic or organic, 1- to 3-valent, anion of an inorganic or organic protonic acid which can form stable salts with amine bases and x can be a number from 1 to 3.

It has been found that $R^5$ can be a linear or branched alkylene group without marked material differences in the final product arising.

Typical examples of the anion X are halide, hydroxide, hypochlorite, sulfate, hydrogen sulfate, nitrite, nitrate, phosphate, dihydrogen phosphate, hydrogen phosphate, carbonate, hydrogen carbonate, chlorate, perchlorate, chromate, dichromate, cyanide, thiocyanate, sulfide, hydrogen sulfide, selenide, telluride, borate, metaborate, azide, tetrafluoroborate, tetraphenylborate, hexafluorophosphate, acetate, propionate, oxalate, trifluoroacetate, trichloroacetate or benzoate.

Typical examples of units of polymeric ammonium compounds according to the invention are

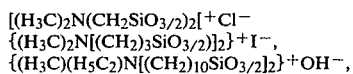

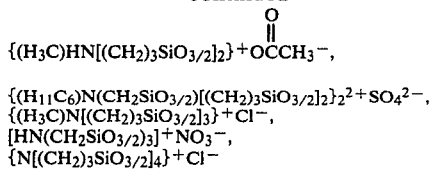

Those polymeric ammonium compounds according to the formula (1) are particularly preferable from the point of view of thermal stability and inertness toward chemical attack, in particular toward bases, as well as in respect of insolubility in which $R^1$, $R^2$ and $R^3$ have the same meaning and in particular $R^1$, $R^2$ and $R^3$ are identical to one another. In a preferred embodiment of the invention $R^1$, $R^2$ and $R^3$ are identical to one another, $R^4$ is methyl and X is chloride, bromide or iodide.

$R^1$ to $R^3$ can be identical to one another and $R^4$ can have the same meaning as $R^1$ to $R^3$ or be identical to $R^1$ and $R^3$ and X can be chloride, bromide or iodide.

There are particular advantages in respect of the availability of the starting materials and the material properties of the polymeric ammonium compound in the case of a compound comprised of polymer units of the formula $$[(H_3C)N(CH_2CH_2CH_2SiO_{3/2})_3]^+Cl^-$$

For the same reasons another advantageous polymeric ammonium compound is comprised of polymer units of the formula

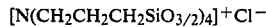

One of the processes for preparing the polymeric ammonium compounds and to which the invention also relates is carried out in practice by using a polymeric amine base which may be crosslinked and/or may have been formed in situ is used as a starting material. This process for preparing polymeric ammonium compounds with a silica-type backbone comprises reacting a polymeric amine base which has been prepared by known processes and is comprised of polymer units of the general formula (3)

in which $R^1$ to $R^3$ have the same scope of meaning as in claim 1, within the course of hours or days with stoichiometric or excess amounts of a linear or branched alkyl halide containing 1-20 C atoms, of a cycloalkyl halide containing 5 to 8 C atoms or of a benzyl halide or with an inorganic or organic protonic acid which can form stable quaternary salts with the amine until all accessible N atoms have been quaternized, separating the resulting polymeric ammonium compound from the liquid phase and drying, if desired with the use of a vacuum, and if desired milling and classifying the remaining solid.

In this process, it has proved advantageous to carry out the quaternization with the use of a suspending medium such as water, alkanes, cycloalkanes, aromatics, cyclic or open-chain ethers, chlorinated hydrocarbons, aliphatic or aromatic nitro compounds, aliphatic or aromatic nitriles or dimethylformamide, dimethyl sulfoxide, acetone, diethyl ketone, methyl ethyl ketone, lower alcohols, such as methanol, ethanol, n- and i-propanol, n-, i- and t-butanol or n-pentanol, or of mixtures thereof, in particular water/alcohol mixtures. The suspending medium should act as a solubilizer, and which is used depends in each case also on the physical properties of the organic halide. The latter, to avoid contamination, should either be gaseous or be at least partially soluble in the solubilizer used.

The quaternization is best carried out below, at or above room temperature up to a temperature of 300° C. under normal pressure or a superpressure which corresponds to the sum of the partial pressures of the individual components of the reaction mixture at the particular temperature. After the quaternization is complete, the solid is freed by conventional techniques, such as filtering, centrifuging and/or decanting or by removal by distillation, if appropriate with the use of a vacuum, of any solvent which may be present or from excess organic halide or from excess protonic acid and is then freed from any residues still adhering by heating under atmospheric pressure or in vacuo. Thereafter drying at temperatures from room temperature to 300° C., if desired with the use of a vacuum, and if desired milling and classifying can be carried out. To increase the stability of the matrix it is frequently advisable to heat-treat the product. This treatment is carried out over a time period of at least one hour up to four days at 200°–400° C. and, if desired, with the use of a vacuum.

A further general process according to the invention for preparing some of the polymeric ammonium compounds starts from monomeric precursors which can be obtained in a manner which is in itself known by quaternizing suitably substituted primary, secondary or tertiary (trialkoxysilylorganyl) (organyl) amines with an organic halide.

This quaternization can be carried out by using pure substances or by using a solubilizer which is preferably of the polar type. It has proved particularly suitable to quaternize the amine by using a solvent, such as cyclic or open-chain ethers, chlorinated hydrocarbon compounds, aliphatic or aromatic nitro compounds, aliphatic or aromatic nitro compounds, aliphatic or aromatic nitriles or dimethylformamide, dimethyl sulfoxide, acetone, diethyl ketone, methyl ethyl ketone, lower alcohols, such as methanol, ethanol, n- and i-propanol, n-, i- and t-butanol or n-pentanol, or mixtures thereof. The resulting quaternary salt, if appropriate after the addition of a crosslinking agent, is then hydrolyzed and condensed, preferably at room temperature to reflux temperature of the reaction mixture.

In one variant of this method, it is possible to proceed in some cases by adding a stoichiometric or excess, relative to complete hydrolysis and condensation, amount of water to the reaction mixture before the quaternization step, since although the amine component and the organic halide component in themselves are soluble in the water/solubilizer mixture the resulting hydrolyzed and polycondensed quaternary salt is insoluble and precipitates. This is particularly the case when a tertiary amine which is substituted by only one trialkoxysilylorganic radical is reacted with a halogenoorganotrialkoxysilane. The quaternization by means of inorganic or organic protonic acids can also be carried out with an aqueous solution of the latter.

The polymeric product obtained in either case can then be worked up analogously to the process mentioned first. It is thus possible to carry out a drying, if desired in vacuo, during which a temperature between room temperature and 300° C. can be used.

The dried product can also be heat-treated, if desired with the use of a vacuum, for at least one hour up to four days at a temperature within a range of 200°–400° C.

The process variants which are most advantageous for processing primary, secondary and tertiary starting amines will be presented in detail below.

In one embodiment the polymeric ammonium compounds with a silica-type backbone are obtained by reacting a primary amine having a substituent comprised of a linear or branched alkylene group having 1 to 10 C atoms or a cycloalkylene group having 5 to 8 C atoms, either group being bonded to a trialkoxysilyl group having alkoxy radicals which contain 1 to 5 C atoms or of a group of the formula:

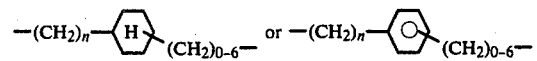

in which n can be a number from 1 to 6 and indicates the number of nitrogen-terminated methylene groups, if appropriate in a solubilizer, with a halogenoorganotrialkoxysilane having alkoxy groups which contain 1 to 5 C atoms and in which the organyl grouping used is a linear or branched alkylene group having 1 to 10 C atoms, a cycloalkylene group having 5 to 8 C atoms or a group of the formula:

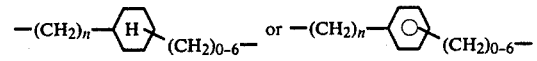

in which n can be a number from 1 to 6 and indicates the number of halogen-terminated methylene groups, hydrolyzing and polycondensing the resulting quaternary salt by reacting it with stoichiometric or excess, relative to quantitative hydrolysis and condensation, amounts of water, if appropriate after prior addition of a solubilizer, preferably in the form of an alcohol which corresponds to the particular alkoxy groups on the Si atoms and/or of a crosslinking agent of the general formula

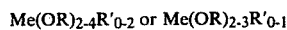

in which Me denotes Si or Ti or Al respectively, R is an alkoxy radical having 1 to 5 C atoms and R' is a methyl or ethyl group, and separating from the liquid phase, drying, if desired with the use of a vacuum, and if desired milling and classifying the product.

A further process starts from a secondary amine and comprises reacting a secondary bis-(trialkoxysilylorgano)-amine with a halogenoorganotrialkoxysilane, the organic groups of which correspond to $R^5$ in the formula (2) or with a linear or branched alkyl halide containing 1 to 20 C atoms, with a cycloalkyl halide containing 5 to 8 C atoms or benzyl halide or with an inorganic or organic protonic acid. For the further working-up, the above-mentioned measures, such as drying, milling, classifying and heat-treating, can be used in any sequence.

A further variant also starts from a secondary amine and proposes quaternizing such an amine having substituents comprised of a trialkoxysilylorgano group and a linear or branched alkyl group containing 1 to 20 C atoms or a cycloalkyl group containing 5 to 8 atoms or a benzyl group with a halogenoorganotrialkoxysilane in which the organic groups correspond to the group $R^5$ in claim 1. Further working-up can be carried out as in the process variant discussed above.

When using a tertiary amine as a starting material, the advantageous embodiments described below can be used. One of these embodiments proposes quaternizing a tertiary tris-(trialkoxysilylorgano)-amine the organic groups of which correspond to the group $R^5$ in claim 1 and the alkoxy groups of which have 1 to 5 C atoms with a linear or branched alkyl halide containing 1 to 20 C atoms or with a cycloalkyl halide containing 5 to 8 C atoms, with a benzyl halide or with an inorganic or organic protonic acid or with a halogenoorganotrialkoxysilane, the organic group of which corresponds to the group $R^5$ in claim 1 and otherwise working up in a manner which corresponds to the measures already discussed.

It is also possible to start from a tertiary amine, the substituents of which are comprised of 2 trialkoxysilylorgano groups the organic groups of which correspond to the group $R^5$ in claim 1 and of a linear or branched alkyl group containing 1 to 20 C atoms or or of a cycloalkyl group containing 5 to 8 C atoms or of the benzyl group, to quaternize with a halogenoorganotrialkoxysilane the organic group of which corresponds to the group $R^5$ in claim 1 or with a linear or branched alkyl halide containing 1 to 20 C atoms, a cycloalkyl halide containing 5 to 8 C atoms or with a benzyl halide or with an inorganic or organic protonic acid and thereafter otherwise to follow with a working-up which corresponds to the measures already presented.

Furthermore, one variant comprises quaternizing a tertiary amine, the substituents of which are comprised of 1 trialkoxysilylorgano group the organic group of which corresponds to the group $R^5$ in claim 1 and of 2 further organic groups which are identical or different to one another in the form of a linear or branched alkyl group containing 1 to 20 C atoms and/or of a cycloalkyl group containing 5 to 8 C atoms and/or of the benzyl group with a halogenoorganotrialkoxysilane, the organic group of which corresponds to the group $R^5$ in claim 1 and otherwise working up by one of the possible methods already discussed.

In all these procedures, the reaction and after-treatment conditions already discussed in the general presentation of the principle of the second process are advantageously used. In particular, drying, if desired in vacuo, can also be carried out at room temperature to 300° C. and it is possible to include, if desired with the use of a vacuum, a heat treatment for a time period of at least one hour to four days at a temperature between 200°–400° C.

In a further process according to the invention all the remaining polymeric ammonium compounds can be prepared which cannot be obtained directly by quaternization (process principle I) or by quaternization and hydrolysis/condensation (process principle II). These compounds include all polymeric ammonium compounds which are completely substituted by organic and organosilyl groups or only by organosilyl groups and additionally have anions other than halide.

Accordingly, this process serves to prepare the polymeric ammonium compounds dealt with above and those polymeric ammonium compounds in which $R^1$ and/or $R^2$ are not hydrogen and in which at the same time the anion is no halide. The process comprises reacting the quaternized, undried, dried and/or heat-treated polymeric ammonium compounds which are completely substituted by organic and organosilyl groups or completely substituted only by organosilyl groups with an inorganic or organic reagent which can dissociate into a cation and an anion for the purpose of mutual exchange of anions according to the static or dynamic ion exchange principle, thereafter washing the solid and, if desired, completely separating the solid from the liquid or even gaseous phase (for example by replacing $Cl^-$ or $I^-$ from HI) and, if desired, drying and in any optional sequence milling, classifying and heat-treating it.

This ion exchange process also includes, in the form of a neutralization, an ion exchange as is possible to carry out by the static or dynamic principle with already known ion exchange resins.

It is also possible to carry out the ion exchange in an agitated suspension of the polymeric starting ammonium compound with the at least partially dissolved reactant. In this step, the insoluble polymeric ammonium compound, in an aqueous suspension or an organic suspending medium of preferably polar type, is brought into contact with the at least partially dissolved reaction component with which the exchange is to be carried out. Thereafter the solid is separated off and, if necessary, stirred again with a fresh solution of the reactant. This step is repeated until quantitative ion exchange is complete. This solid can then be separated off by conventional techniques, such as filtering, centrifuging and/or decanting, washed until salt-free and dried at room temperature or an elevated temperature up to 300° C., if desired with the use of a vacuum, heat-treated at a temperature of 200°–400° C., milled and classified.

If the dynamic principle is used, the polymeric starting ammonium compound is used as an ion exchange bed and brought into contact with the solution of the at least partially dissolved reactant. Here also, as in the case of the products obtained by the static method, after-treatment within the range mentioned can be provided.

In general, the treatment steps additionally carried out after the drying can be carried out in any sequence or can be partially omitted.

If an ion exchange column is used as ion exchange bed, the polymeric starting product, to ensure an adequate flow rate, must have a certain minimum particle size which must also be adapted to the size of the column. In general, a minimum particle size of 0.2 mm will prove adequate for laboratory columns. After ion exchange is complete, in this case washing is also carried out until salt-free and thereafter either after-treatment measures or further ion exchange measures can be carried out. The polymeric ammonium compounds can, of course, be milled not only in the dry state but also when wet, directly after or before the quaternization or after the polycondensation.

The fact that the polymeric ammonium compounds can be used for anion exchange is the basis for the most important application of these new products, namely the use as universally applicable anion exchange materials which in addition to having the advantages of a very heat- and solvent-resistant matrix, of strongly fixed ammonium groups which are inert toward dissolving away, the non-swellability in an aqueous or organic medium, the applicability in organic media, the good weight capacity and the very good volume capacity, also have the advantage that, they can be converted into the hydroxide form with ammonia, the latter point being a feature which is possible only to a very small extent in the case of known ion exchange materials.

Accordingly, the invention also relates to the use of the polymeric ammonium compounds as anion exchange materials.

The new polymeric ammonium compounds described can be characterized in particular by means of the mass balances in their preparation (hydrolysis and condensation is always carried to completion), elemental analyses, which usually correspond very exactly to the stoichiometry, and by means of results obtained when using them as an anion exchange material. Their decomposition points are in air at far about 200° C. and in a protective gas atmosphere at about 400° C. Depending on the pretreatment, the polymeric ammonium compounds have surface areas of 0.1 to 2,000 m²/g and particle size diameters of about 1 cm to 1 μm. A particle size range of 0.1–1.5 mm, as required for commercial use as ion exchange material, can be selected without difficulty.

Below, the invention is illustrated in more detail by means of illustrative examples in respect of the particular preparation variants according to the invention while using the starting materials which in principle are most important.

EXAMPLE 1

2,093.20 g (6.3 moles) of $I\text{-}CH_2CH_2CH_2Si(OC_2H_5)_3$ were added in the course of 1 hour at approximately room temperature to a solution of 218.73 g (7.04 moles) of $CH_3NH_2$ in 1,700 ml of ethanol, and the resulting mixture was then heated under reflux for 20 hours. The reaction mixture was then cooled down to 50° C., a solution of 574.89 g (8.45 moles) of $NaOC_2H_5$ in 3 liters of ethanol was added in the course of 1 hour, and the resulting mixture was stirred for a further 2 hours under reflux. After the alcohol present and excess methylamine had been removed by distillation in a rotary evaporator, 1.5 liters of diethyl ether were added, and the sparingly soluble salts were filtered off with suction and washed with 250 ml of diethyl ether, and the diethyl ether in turn was removed by distillation. The remaining liquid was initially separated from a small amount of a second phase which was present in the form of a viscous oil at the bottom of the vessel and then subjected to fractional distillation. The desired product $H_3CN[CH_2CH_2CH_2Si(OC_2H_5)_3]_2$ distilled over under a pressure of 0.8 mbar at a temperature of 150°–152° C. The yield, calculated according to Equations (I) and (II) above, was 983.48 g and thus 71% of theory. The product was dissolved in 1 liter of ethanol, and 1 liter of demineralized water was added with gentle stirring in the course of 15 minutes at 50°–55° C. to the solution. The mixture was then heated up to reflux temperature and the contents instantaneously solidified into a pudding-like material which, in the course of a further 3 hours of stirring, was dispersed to give a finely divided suspension. The solid was then filtered off and washed several times with a total of 5 liters of water, and the product was dried for 12 hours at 150° C./100 mbar and milled in a Pin mill. Complete hydrolysis and condensation of the monomer product used would produce 486.15 g of polymeric product; 485.2 g were in fact obtained, this corresponds to 99.8% of theory.

293.9 g of methyl iodide were added in the course of 30 minutes to a suspension of 150.0 g of this polymeric amine, comprised of units of the formula $(H_3C)N(CH_2CH_2CH_2SiO_{3/2})_2$, in 500 ml of toluene, and the mixture was then stirred for 24 hours under reflux. The solid was centrifuged off, washed with 2×150 ml of toluene, and dried for 12 hours at 150° C./100 mbar. 236.5 g (95.4% of theory) of a polymeric ammonium compound, comprised of units of the formula $[(H_3C)_2N(CH_2CH_2CH_2SiO_{3/2})_2]^+I^-$, were obtained. This formula was confirmed by a comparison of the expected and the actually found analytical values.

| Analytical data: | % of C | % of H | % of N | % of Si | % of I |
|---|---|---|---|---|---|
| Theory: | 26.74 | 5.05 | 3.90 | 15.63 | 35.32 |
| Found: | 25.66 | 5.55 | 3.82 | 14.71 | 33.03 |

EXAMPLE 2

493.58 g (2.32 moles) of chloromethyltriethoxysilane were added in the course of 2 hours with stirring at 50° C. to 300 g (2.32 moles) of octylamine. The mixture was then stirred for 30 hours at 180° C. and then cooled down to room temperature, and 157.88 g (2.32 moles) of $NaOC_2H_5$, dissolved in 1 liter of ethanol, were added in the course of 30 minutes. The resulting mixture was stirred for a further 2 hours at reflux temperature, and the alcohol present was then distilled off, and the solids were filtered off and washed with n-hexane, and the n-hexane in turn was removed by distillation. The remaining liquid was charged into a thin-film evaporator in which, at a heating jacket temperature of 120° C. and under a vacuum of 0.8 mbar, the octylamine liberated in the deprotonation and small amounts of other readily volatile contaminants were removed overhead.

The resulting bottom product was directly mixed with 0.6 liter of toluene, the resulting mixture was heated to 60° C., and 500 ml of water were added with stirring in the course of 20 minutes. Stirring was continued for a further 1 hour at the same temperature, during which period a yellowish-white precipitate was formed. This was then stirred for a further 4 hours at the reflux temperature, then filtered off and washed first with ethanol and then with a lot of water and finally dried for 24 hours at 120° C./100 mbar. 306.99 g (102.0% of theory) of a polymeric product composed of units of the formula $C_8H_{17}N[CH_2SiO_{3/2}]_2$ were obtained.

200 g of this polymeric base were first milled in a pin mill and then combined with 744.4 g of 1-bromooctane. This mixture was then stirred for 52 hours at 130°–140° C. The solid was centrifuged down, washed 3× with a total of 1 liter of diethyl ether and dried for 24 hours at 130° C./100 mbar. 328.7 g (94.2% of theory) of a polymeric product comprised of units of the formula $[(C_8H_{17})_2N(CH_2SiO_{3/2})_2]^+Br^-$ were obtained.

| Analytical data: | % of C | % of H | % of N | % of Si | % of Br |
|---|---|---|---|---|---|
| Theory: | 47.77 | 8.46 | 3.09 | 12.41 | 17.66 |
| Found: | 46.32 | 8.22 | 3.21 | 13.21 | 16.02 |

EXAMPLE 3

160.0 g of a polymeric amine prepared from benzylamine and

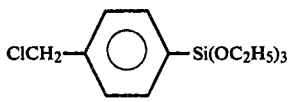

in a manner analogous to Example 2, milled in a pin mill, and comprised of units of the formula

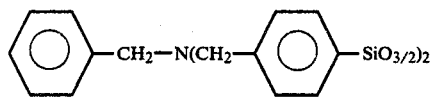

and 204.0 g of methyl iodide were stirred for 43 hours under reflux in 350 ml of monoethylene glycol dimethyl ether.

The solid was then centrifuged down, washed with 2×200 ml of monoethylene glycol dimethyl ether and dried for 12 hours at 120° C./100 mbar. 214.2 g (98.3% of theory) of a polymeric ammonium compound, comprised of units of the formula

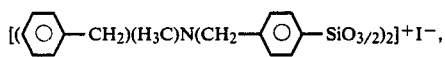

were obtained.

| Analytical data: | % of C | % of H | % of N | % of Si | % of I |
|---|---|---|---|---|---|
| Theory: | 49.72 | 4.17 | 2.64 | 10.57 | 23.88 |
| Found: | 47.89 | 4.02 | 2.89 | 8.99 | 22.10 |

EXAMPLE 4

993.6 g (5.0 moles) of Cl—CH$_2$CH$_2$C$_2$Si(OCH$_3$)$_3$ were added dropwise at room temperature in the course of 1.5 hours to 896.4 g (5.0 moles) of H$_2$N—CH$_2$CH$_2$CH$_2$Si(OCH$_3$)$_3$. The mixture was then heated to 150° C., stirred for 15 hours at this temperature, and then cooled down to room temperature, and then first 1 liter of dried methanol and then 270.1 g (5.0 moles) of NaOCH$_3$, in portions, were added. After a further 3 hours of stirring under reflux, the sodium chloride formed was filtered off. The latter was then washed out with a total of 800 ml of methanol. After the washings had been combined with the product mixture, the methanol was removed by distillation at a bottom temperature of 60°–80° C. and under a pressure of 50 mbar, and the remaining liquid was charged into a Sambay evaporator. 402.5 g of H$_2$N—CH$_2$CH$_2$CH$_2$Si(OCH$_3$)$_3$ were recovered as top product. 1 liter of methanol was added to the bottom product, and the resulting mixture was heated with stirring to 50° C. 2 liters of water were then added in the course of 30 minutes. After only a part of the water had been added, spontaneous polycondensation of the amine commenced. The mixture was heated with slow stirring to the reflux temperature and refluxed for 2 hours.

After the mixture had been cooled down to room temperature, a submersion tube was introduced into the reaction vessel through which, at a bottom temperature of 70° C., a total of 500 g of methyl chloride were passed into the reaction mixture in the course of 20 hours. The solid was then filtered off with suction, washed with 1 liter of demineralized water, dried for 12 hours in a vacuum oven at 150° C./80 mbar, then milled in a hammer mill and classified into the particle size ranges 0.25–0.50 mm, 0.1–0.25 mm and <0.1 mm. The total weight was 877.9 g (101.2% of theory) of a polymeric ammonium compound comprised of units of the formula [(H$_3$C)N(CH$_2$CH$_2$CH$_2$SiO$_{3/2}$)$_3$]$^+$Cl$^-$.

| Analytical data: | % of C | % of H | % of Si | % of N | % of Cl |
|---|---|---|---|---|---|
| Theory: | 34.61 | 6.10 | 24.28 | 4.04 | 10.22 |
| Found: | 32.13 | 6.59 | 23.35 | 4.41 | 10.76 |

The particle size fraction of the product of 0.25–0.5 mm had a specific surface area of 80 m$^2$/g. According to a DSC investigation, a sample of the product decomposed at a temperature of 241° C. in air and at a temperature of 416° C. in a protective gas atmosphere.

EXAMPLE 5

100 g of the polymeric base comprised of units of the formula N(CH$_2$CH$_2$CH$_2$SiO$_{3/2}$)$_3$ and prepared in a manner analogous to Example 4 were combined with 277.0 g of i-butyl bromide in 500 ml of toluene. The mixture was stirred for 6 days under reflux and thereafter worked up in a manner analogous to Example 1. 129.9 g (88.9% of theory) of a polymeric ammonium compound comprised of units of the formula [(H$_3$C)$_2$CH—CH$_2$—N(CH$_2$CH$_2$CH$_2$SiO$_{3/2}$)$_3$]$^+$Br$^-$ were obtained.

| Analytical data: | % of C | % of H | % of Si | % of N | % of Br |
|---|---|---|---|---|---|
| Theory: | 36.02 | 6.28 | 19.44 | 3.23 | 18.43 |
| Found: | 34.49 | 6.08 | 18.94 | 3.49 | 15.81 |

EXAMPLE 6

150 g of a polymeric amine comprised of units of the formula

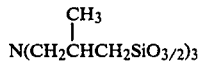

and prepared in a manner analogous to Example 4 were heated under reflux for 15 hours together with 120.0 g of benzyl chloride in 400 ml of toluene. The product was then worked up in a manner analogous to Example 1. 203.0 g (98.5% of theory) of a polymeric ammonium compound comprised of units of the formula

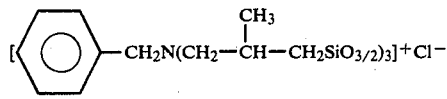

were obtained.

| Analytical data: | % of C | % of H | % of Si | % of N | % of Cl |
|---|---|---|---|---|---|
| Theory: | 49.06 | 6.72 | 18.11 | 3.01 | 7.62 |
| Found: | 48.28 | 6.48 | 17.22 | 3.09 | 7.55 |

EXAMPLE 7

75 g of a polymeric base comprised of units of the formula

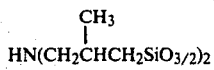

and prepared by polycondensation of the monomer product

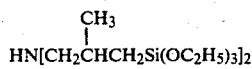

and 150.0 g of cyclohexyl bromide were heated for 48 hours under reflux in 100 ml of toluene. After the product had been worked up as in Example 1, 123.8 g (96.9% of theory) of a polymeric ammonium compound having units of the formula

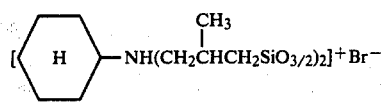

were obtained.

| Analytical data: | % of C | % of H | % of Si | % of N | % of Br |
|---|---|---|---|---|---|
| Theory: | 42.63 | 7.16 | 14.24 | 3.55 | 20.26 |
| Found: | 41.98 | 7.32 | 13.41 | 3.72 | 19.95 |

EXAMPLE 8

1,204 g (5.0 moles) of Cl—$CH_2CH_2CH_2Si(OC_2H_5)_3$ and 284.4 g (16.7 moles) of liquid $NH_3$ were reacted for 24 hours at 150° C. in a lift autoclave. The ammonium chloride formed was filtered off and washed out with a total of 300 ml of n-hexane. After the washings and filtrate had been combined, n-hexane was first removed in a rotary evaporator. The remaining bottom product was charged into a thin-film evaporator in which, at a jacket temperature of 150° C. and under a pressure of 0.8 mbar, readily volatile constituents were removed. 760.0 g of $N[CH_2CH_2CH_2Si(OC_2H_5)_3[_3$ remained as sparingly volatile fraction to which 750 ml of ethanol and 251.3 g of $Si(OC_2H_5)_4$ were added. After heating up to 70° C., 1 liter of water was added in the course of 1 hour with slow stirring. The mixture was stirred for a further 1 hour at this temperature and then for 3 hours under reflux. The resulting tertiary, crosslinked amine was then quaternized by passing through a total of 300 g of methyl chloride and worked up in a manner analogous to Example 4. 501.3 g (102.1% of theory) of a polymeric crosslinked ammonium compound having units of the formula $[(H_3C)N(CH_2CH_2CH_2SiO_{3/2})_3]^+Cl^-$. $SiO_2$ were obtained.

| Analytical data: | % of C | % of H | % of Si | % of N | % of Cl |
|---|---|---|---|---|---|
| Theory: | 29.51 | 5.20 | 27.60 | 3.44 | 8.71 |
| Found: | 28.15 | 5.62 | 25.91 | 3.80 | 8.88 |

The particle size fraction of the product of 0.25–0.5 mm particle size diameter, according to a surface area determination on an Areameter, had a specific surface area of 233 m²/g. An investigation by differential scanning calorimetry showed the start of an exothermic decomposition at 238° C. in air and an endothermic decomposition at 428° C. in an $N_2$ atmosphere.

EXAMPLE 9

A mixture of 20 g of the milled, polymeric base comprised of units of the formula $N[CH_2CH_2CH_2SiO_{3/2}]_3$ and prepared in accordance with Example 4 and 200 ml of a 1 N HCl solution were stirred for 4 hours at room temperature in a beaker. The solid was then filtered off, washed with demineralized water until neutral and dried for 12 hours at 120° C./80 mbar. 22.4 g (99.7% of theory) of a polymeric ammonium compound having units of the formula $[NH(CH_2CH_2CH_2SiO_{3/2})_3]^+Cl^-$ were obtained.

| Analytical data: | % of C | % of H | % of Si | % of N | % of Cl |
|---|---|---|---|---|---|
| Theory: | 32.47 | 5.75 | 25.31 | 4.21 | 10.65 |
| Found: | 31.28 | 5.89 | 23.96 | 4.56 | 10.55 |

EXAMPLE 10

The treatment of 20 g of a polymeric base comprised of units of the formula $N(CH_2CH_2CH_2SiO_{3/2})_3$ with 200 ml of 1 N acetic acid in a manner analogous to Example 9 quantitatively produced a polymeric ammonium compound having units of the formula:

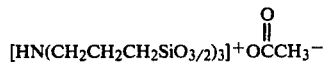

| Analytical data: | % of C | % of H | % of Si | % of N |
|---|---|---|---|---|
| Theory: | 37.05 | 6.22 | 23.63 | 3.93 |
| Found: | 35.89 | 6.35 | 21.97 | 4.16 |

EXAMPLE 11

1,137.5 g (95.1% of theory) of a polymeric product comprised of polymer units of the formula:

and obtained from 1,075.7 g (6.0 moles) of $H_2N$—$CH_2CH_2CH_2Si(OCH_3)_3$, 1,192.3 g (6.0 moles) of Cl—$CH_2CH_2CH_2Si(OCH_3)_3$ and 444.8 g (3.0 moles) of $(CH_2H_5)_2Si(OCH_3)_2$ in a manner analogous to Examples 4 and 8 were suspended in 2 liters of toluene. At the reflux temperature, a total of 989.2 g of methyl chloride were passed in the course of 20 hours. After working up as in Example 1, 1,245.7 g (97.2% of theory) of a polymeric product having units of the formula $[(H_3C)N(CH_2CH_2CH_2SiO_{3/2})_3]^+Cl^-$. $(CH_2H_5)_2SiO$ were obtained.

| Analytical data: | % of C | % of H | % of Si | % of N | % of Cl |
|---|---|---|---|---|---|
| Theory: | 37.43 | 6.96 | 25.01 | 3.12 | 7.89 |
| Found: | 36.59 | 7.42 | 23.85 | 3.48 | 8.11 |

EXAMPLE 12

53.8 g (0.3 mole) of $H_2N$—$(CH_2)_3$—$Si(OCH_3)_3$ were added dropwise in the course of 30 minutes to a hot solution at 80° C. of 125.3 g (0.40 mole) of Br—$(CH_2)_8$—$Si(OCH_3)_3$ in 150 ml of ethanol. The mixture was stirred for a further hour under reflux, and 200 ml of water were then added dropwise in the course of 30 minutes to the clear solution which had cooled down to 30° C. The precipitate formed in the course of a further 2 hours of stirring was filtered off, washed with 3×100 ml of ethanol and 0.5 liter of water and then dried for 8 hours at 120° C./80 mbar.

94.7 g (89.1% of theory) of a polymeric ammonium compound having units of the formula:

were obtained.

| Analytical data: | % of C | % of H | % of Si | % of N | % of Br |
|---|---|---|---|---|---|
| Theory: | 37.28 | 6.83 | 15.85 | 3.95 | 22.55 |
| Found: | 36.72 | 7.21 | 13.99 | 3.97 | 21.28 |

EXAMPLE 13

101.1 g (0.35 mole) of

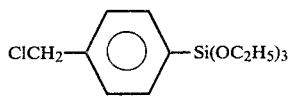

and 94.3 g (0.35 mole) of

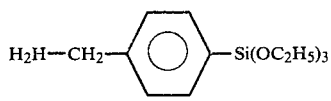

were reacted in a manner analogous to Example 12. Before water was added to the solution of the monomer compound

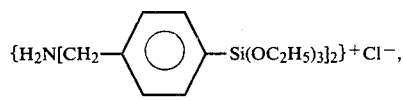

which had cooled down to room temperature, 79.8 (0.35 mole) of $Ti(OC_2H_5)_4$ were added to the latter. The further procedure followed was as in Example 12. It was possible in this way to obtain 132.7 g (91.2% of theory) of a polymeric ammonium compound comprised of units of the approximate formula

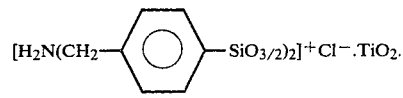

| Analytical data: | % of C | % of H | % of Si | % of N | % of Cl | % of Ti |
|---|---|---|---|---|---|---|
| Theory: | 40.44 | 3.39 | 13.51 | 3.37 | 8.53 | 11.52 |
| Found: | 38.19 | 3.17 | 12.28 | 3.57 | 7.98 | 10.95 |

EXAMPLE 14

148.0 g (0.51 mole) of $I-CH_2CH_2CH_2Si(OCH_3)_3$ were dissolved in 100 ml of methanol. 170.8 g (0.5 mole) of $HN[CH_2CH_2CH_2Si(OCH_3)_3]_2$ were added dropwise in the course of 1 hour with stirring to the solution which had been heated to reflux temperature. After the addition was complete, stirring was continued for a further hour under reflux.

After the solution had cooled down to room temperature, 200 ml of water were then added in the course of 30 minutes, and stirring was continued for a further 2 hours. The precipitate formed was filtered off, washed with methanol and water and dried for 24 hours at 120° C./100 mbar. 196.3 (92.5% of theory) of the expected polymeric ammonium compound having units $[HN(CH_2CH_2CH_2SiO_{3/2})_3]^+I^-$ were obtained.

| Analytical data: | % of C | % of H | % of Si | % of N | % of I |
|---|---|---|---|---|---|
| Theory: | 25.47 | 4.51 | 19.85 | 3.30 | 29.90 |
| Found: | 24.86 | 5.35 | 18.25 | 3.59 | 27.71 |

EXAMPLE 15

250 ml of a 2 N aqueous HCl solution were added with stirring in the course of 1 hour at room temperature to a solution of 100 g (0.22 mole) of the monomer product

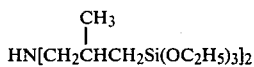

in 100 ml of ethanol. Stirring was continued for a further 3 hours at room temperature, and the resulting solid was then filtered off, washed with 4 liters of water until acid-free and then dried for 8 hours at 130° C./80 mbar. 56.8 g (96.4% of theory) of a polymeric ammonium compound having units of the formula:

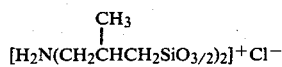

were obtained.

| Analytical data: | % of C | % of H | % of Si | % of N | % of Cl |
|---|---|---|---|---|---|
| Theory: | 35.87 | 6.77 | 20.97 | 5.23 | 13.24 |
| Found: | 35.02 | 6.90 | 20.11 | 5.56 | 12.96 |

EXAMPLE 16

138.2 g (0.40 mole) of

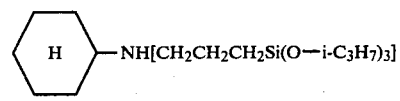

were added with vigorous stirring in the course of 2 hours to 150.6 g (0.46 mole) of hot $Br-CH_2CH_2CH_2Si(O-i-C_3H_7)_3$ at 100° C. Stirring was continued for a further 2 hours at this temperature, and the mixture was then cooled down to room temperature, and at first 300 ml of isopropanol and then 200 ml of water were added in the course of 1 hour. Stirring was continued for a further 2 hours, and the solid formed was then centrifuged off, washed at first with 2×200 ml of isopropanol and then with 1 liter of water, dried at 120° C./100 mbar for 24 hours and then heat-treated for 5 hours at 200° C./100 mbar. 133.7 g (91.2% of theory) of a polymeric ammonium compound comprised of units of the formula

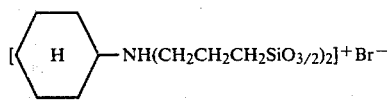

were obtained.

| Analytical data: | % of C | % of H | % of Si | % of N | % of Br |
|---|---|---|---|---|---|
| Theory: | 39.34 | 6.60 | 15.33 | 3.82 | 21.81 |
| Found: | 38.70 | 6.51 | 13.90 | 3.97 | 20.17 |

EXAMPLE 17

73.6 g (0.40 mole) of n-butyl iodide were added in the course of 2 hours with stirring to 201.5 g (0.4 mole) of hot $N[CH_2CH_2CH_2Si(OCH_3)_3]_3$ at 130° C. After the addition was complete, stirring was continued for a further 8 hours at 150° C., and the mixture was then cooled down to room temperature. After the addition of 300 ml of methanol, 200 ml of water were added dropwise in the course of 30 minutes to the clear solution. Stirring was continued for a further 1 hour at room temperature and 2 hours under reflux, and the solid formed was then milled in suspension by means of a disperser, centrifuged off, washed with a total of 2 liters of water, dried for 12 hours at 180° C. and heat-treated for 12 hours at 250° C./100 mbar.

184.3 g (95.9% of theory) of a polymeric ammonium compound having units of the formula $[(C_4H_9)N(CH_2CH_2CH_2SiO_{3/2})_3]^+I^-$ were obtained.

| Analytical data: | % of C | % of H | % of Si | % of N | % of I |
|---|---|---|---|---|---|
| Theory: | 32.49 | 5.66 | 17.53 | 2.91 | 26.41 |
| Found: | 30.91 | 5.76 | 15.99 | 3.28 | 25.62 |

EXAMPLE 18

63.6 g (0.32 mole) of $Cl-CH_2CH_2CH_2Si(OCH_3)_3$ were added in the course of 30 minutes with stirring to 161.3 g (0.32 mole) of hot $N[CH_2CH_2CH_2Si(OCH_3)_3]_3$ at 150° C. Stirring was carried out at this temperature for a further 48 hours, and the viscous liquid was then cooled down to room temperature, and, after the addition of 200 ml of methanol and 300 ml of water and a further 3 hours' heating under reflux, the polymeric product was centrifuged off, washed with 2 liters of water, dried for 5 hours at 150° C. and heat-treated for 12 hours at 300° C./10 mbar. 122.3 g (89.7% of theory) of a polymeric ammonium compound comprised of units of the formula $[N(CH_2CH_2CH_2SiO_{3/2})_4]^+Cl^-$ were obtained.

| Analytical data: | % of C | % of H | % of Si | % of N | % of Cl |
|---|---|---|---|---|---|
| Theory: | 33.82 | 5.68 | 26.36 | 3.29 | 8.32 |
| Found: | 31.97 | 6.15 | 25.70 | 3.68 | 7.34 |

EXAMPLE 19

226.3 g (97.4% of theory) of a polymeric ammonium compound having units of the formula $[(H_3C)N(CH_2CH_2CH_2SiO_{3/2})_3]^+I^-$ were prepared from 188.4 g (0.53 mole) of $(H_3C)N[CH_2CH_2CH_2Si(OCH_3)_3]_2$ and 153.8 g (0.53 mole) of $I-CH_2CH_2CH_2Si(OCH_3)_3$ in a manner analogous to Example 17.

| Analytical data: | % of C | % of H | % of Si | % of N | % of I |
|---|---|---|---|---|---|
| Theory: | 27.39 | 4.83 | 19.22 | 3.19 | 28.94 |
| Found: | 28.04 | 5.59 | 18.87 | 3.74 | 27.53 |

EXAMPLE 20

The experiment according to Example 19 was repeated. Before the hydrolysis and polycondensation, 8.59 g (0.053 mole) of $Al(OC_2H_5)_3$ were added to the solution of the monomeric ammonium compound. After the further procedure followed was in other respects as in Example 19, a crosslinked polymeric ammonium compound having units of the formula $[(H_3C)N(CH_2CH_2CH_2SiO_{3/2})_3]^+I^-$. 0.1 $AlO_{3/2}$ was obtained. Yield: 233.2 g (99.2% of theory).

| Analytical data: | % of C | % of H | % of Si | % of N | % of I | % of Al |
|---|---|---|---|---|---|---|
| Theory: | 27.08 | 4.77 | 19.00 | 3.16 | 28.61 | 0.61 |
| Found: | 26.58 | 4.61 | 17.97 | 3.29 | 27.35 | 0.54 |

EXAMPLE 21

257.8 g (1.06 moles) of $Br-CH_2CH_2CH_2Si(OCH_3)_3$ were added in the course of 1.5 hours with stirring to 220 g (1.06 moles) of hot $(H_3C)_2NCH_2CH_2CH_2Si(OCH_3)_3$ at 130° C. The mixture was reacted for a further 6 hours at this temperature and thereafter cooled down to room temperature, and at first 300 ml of methanol and finally, in the course of 30 minutes. 200 ml of water were added, and stirring was continued for a further 2 hours. The solid formed was further treated as in Example 17. 299.3 g (90.4% of theory) of a polymeric ammonium compound having units of the formula $[(H_3C)_2N(CH_2CH_2CH_2SiO_{3/2})_2]^+Br^-$ were obtained.

| Analytical data: | % of C | % of H | % of Si | % of N | % of Br |
|---|---|---|---|---|---|
| Theory: | 30.77 | 5.81 | 17.99 | 4.48 | 25.58 |
| Found: | 29.14 | 5.64 | 16.20 | 4.56 | 24.77 |

EXAMPLE 22

25 g of the polymeric ammonium compound having units of the formula $[(H_3C)N(CH_2CH_2CH_2SiO_{3/2})_3]^+Cl^-$ and prepared according to Example 1 were milled in a pin mill. 20 g of this milled product (52.05 moles of $I^-$ according to $I^-$ analysis) were reacted in 5 batches with a total of 2,212 g of a 2% strength $NaNO_3$ solution (520.5 moles of $NO_3^-$). This reaction was carried out by stirring the polymeric ammonium iodide, in a beaker, 5 times with 442.4 g each time of this $NaNO_3$ solution and for 15 minutes each, the supernatant solution was then decanted, and fresh $NaNO_3$ solution was added to the remaining solid. At the end of the multistage reaction, the solid was washed with 2 times 100 ml of water, dried for 5 hours at 130° C./100 mbar, and analyzed.

| Analytical data: | % of C | % of H | % of Si | % of I | % of NO₃⁻ |
|---|---|---|---|---|---|
| Before NO₃⁻ exchange | 25.66 | 5.55 | 14.71 | 33.03 | — |
| After NO₃⁻ exchange | 31.42 | 6.09 | 18.28 | 0.81 | 20.11 |

Quantitative I⁻/NO₃⁻ exchange and the subsequent presence of a polymeric ammonium compound having units of the formula [(H₃C)₂N(CH₂CH₂CH₂SiO₃/₂)₂]⁺NO₃⁻ would produce the following analytical data:

| % of C | % of H | % of Si | % of I | % of NO₃⁻ |
|---|---|---|---|---|
| 32.64 | 6.16 | 19.08 | 0 | 21.06 |

According to the analytical data found an approximately 95–98% I⁻/NO₃⁻ exchange has thus taken place. This result was confirmed by means of an I⁻ determination on the combined decanted solutions, since these contained 96.7% of the iodide originally present on the 20 g of starting polymer.

EXAMPLE 23

An ion exchange column having a diameter of 25 mm was filled with 50 g of the polymeric ammonium compound prepared according to Example 4 and having a particle size of 0.25–0.5 mm and a Cl⁻ content of 10.76%. The level of polymer, not only in the dry state but also in the subsequent state when the column has been filled with water, was about 30 cm. 10 times the molar amount of ammonia, relative to the chloride present on the solid and a total of 5.38 g (151.75 moles) was passed in 5 batches in the form of a 1% strength NH₃ solution (a total of 2,584.5 g) through this column. After the ion exchange material had been washed out with water until the liquid passed through the column showed a neutral reaction, the washings and the 5 batches which had passed through were combined, and the mixture was concentrated by evaporating water and a chloride determination was carried out on the clear concentrate. According to this determination, a total of 5.35 g (150.9 moles) of chloride were present in solution, which corresponds to a 99.4% Cl⁻/OH⁻ exchange.

EXAMPLE 24

10 times the molar amount of hydrochloric acid, relative to hydroxide present on the solid, was passed in turn in 5 batches in the form of a 5% strength HCl solution (a total of 1,100.4 g of solution) through the column of Example 23 filled with ion exchange material present in the OH⁻ form. After the subsequent washing of the column contents with water until a neutral reaction was shown by the liquid passed through the column, a sample was taken from the column contents and investigated, after drying, for its chloride content. The analysis showed a Cl⁻ content of 10.55%, so that the OH⁻/Cl⁻ exchange carried out had taken place virtually quantitatively.

EXAMPLE 25

50 g of the crosslinked polymeric ammonium compound prepared according to Example 8 and comprised of units of the formula [(H₃C)N(CH₂CH₂CH₂SiO₃/₂)₃]⁺Cl⁻·SiO₂ and having a particle size of 0.25–0.5 mm and a Cl⁻ content of 8.88% were treated, in a manner analogous to Example 23, with 5 times the molar amounts of Na₂SO₄, relative to chloride present on the solid, a total of 4.44 g, in the form of a 5% strength Na₂SO₄ solution (a total of 1,778.8 g). According to a Cl⁻ analysis on the combined amounts of liquid which had passed through the column, a 98.9% Cl⁻/SO₄²⁻ exchange had taken place.

We claim:

1. A polymeric ammonium compound with a silica-type backbone, comprising units of the general formula

in which $R^1$ and $R^2$ represent a group of the general formula (2)

in which $R^5$ is linear or branched alkylene having 1 to 10 C atoms, cycloalkylene having 5 to 8 C atoms,

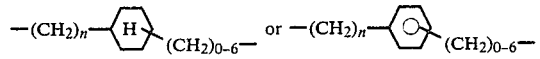

in which n is a number from 1 to 6 and indicates the number of nitrogen-terminated methylene groups, and $R^1$ and $R^2$ can be the same or different, and the free valencies of the oxygen atoms are saturated either by silicon atoms of further groups of the formula (2) and/or by crosslinking bridge members of the formula:

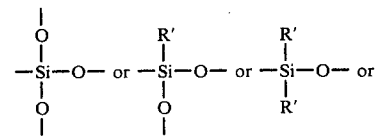

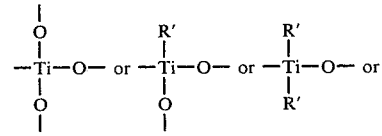

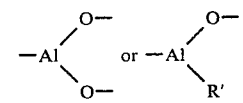

in which
$R'$ is methyl or ethyl and the ratio of the silicon atoms in (2) to the bridge atoms silicon, titanium and aluminum is 1:0 to 1:10,
$R^3$ and $R^4$ can have the same scope of meaning as $R^1$ and $R^2$ or represent hydrogen, a linear or brached alkyl containing 1 to 20 C atoms, cycloalkyl containing 5 to 8 C atoms or the benzyl group and R³ and R⁴ can be identical or different and be identical or different to R¹ and/or R², X represents an inorganic or organic, 1- to 3-valent anion of an inorganic or organic protonic acid which forms stable salts with amine bases and x is a number from 1 to 3.

2. A polymeric ammonium compound in claim 1 wherein X represents halide, hydroxide, hypochlorite, sulfate, hydrogen sulfate, nitrite, nitrate, phosphate, dihydrogen phosphate, hydrogen phosphate, carbonate, hydrogen carbonate, chlorate, perchlorate, chromate, dichromate, cyanide, thiocyanate, sulfide, hydrogen sulfide, selenide, telluride, borate, metaborate, azide, tetrafluoroborate, tetraphenylborate, hexafluorophosphate, acetate, propionate, oxalate, trifluoroacetate, trichloroacetate or benzoate.

3. A polymeric ammonium compound as claimed in claim 1, wherein R¹, R² and R³ are identical to one another, R⁴ is methyl and X is chloride, bromide or iodide.

4. A polymeric ammonium compound as claimed in claim 1, wherein R¹ to R³ are identical to one another and R⁴ has the same meaning as R¹ to R³ or is identical to R¹ or R³ and X is chloride, bromide or iodide.

5. A polymeric ammonium compound as claimed in claim 1, comprising polymer units of the formula:

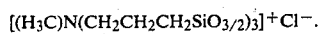

6. A polymeric ammonium compound as claimed in claim 1, comprising polymer units of the formula:

7. A process for preparing a polymeric ammonium compound with a silica-type backbone as claimed in claim 1, comprising reacting a polymeric amine base which is comprised of polymer units of the general formula (3)

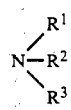

in which R¹ and R³ have the same scope of meaning as in claim 1, with stoichiometric or excess amounts of a linear or branched alkyl halide containing 1-20 C atoms, of a cycloalkyl halide containing 5 to 8 C atoms or of a benzyl halide or with an inorganic or organic protonic acid which forms stable quaternary salts with the amine until all accessible N atoms have been quaternized, separating the resulting polymeric ammonium compound from the liquid phase.

8. The process of claim 7, wherein the polymeric ammonium compound is dried.

9. The process of claim 7, wherein the product is milled and classified.

10. The process for preparing a polymeric ammonium compound, as claimed in claim 7, wherein the quaternization is carried out with the use of a suspending medium.

11. The process of claim 10, wherein water and alcohol mixtures are used.

12. The process for preparing a polymeric ammonium compound as claimed in claim 7, wherein the quaternization is carried out below, at or above room temperature up to a temperature of 300° C. under normal pressure or an over-pressure which corresponds to the sum of the partial pressures of the individual components of the reaction mixture at the particular temperature.

13. A process for preparing a polymeric ammonium compound with a silica-type backbone, as claimed in claim 1, comprising reacting a primary amine having a substituent comprised of a linear or branched alkylene group having 1 to 10 C atoms, a cycloalkylene group having 5 to 8 C atoms,

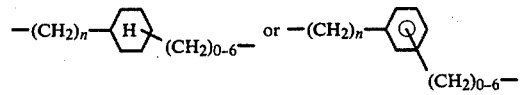

in which n is a number from 1 to 6 and indicates the number of nitrogen-terminated methylene groups, being bonded to a trialkoxysilyl group having alkoxy radicals which contain 1 to 5 C atoms, with a halogenoorganotrialkoxysilane having alkoxy groups which contain 1 to 5 C atoms and in which the organic grouping used is a linear or branched alkylene group having 1 to 10 C atoms, a cycloalkylene group having 5 to 8 C atoms,

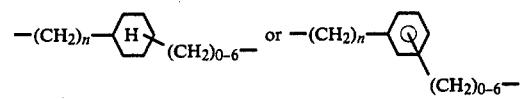

in which n is a number from 1 to 6 and indicates the number of halogen-terminted methylene groups, hydrolyzing and polycondensing the resulting quaternary salt by reacting it with stoichiometric or excess, relative to quantitative hydrolysis and condensation, amounts of water, and separating the product from the liquid phase.

14. The process of claim 13, wherein a solubilizer is present in the reaction.

15. The process of claim 14, wherein the solubilizer is an alcohol which corresponds to the particular alkoxy groups on the Si atoms.

16. The process of claim 13, wherein a crosslinking agent is added of the formula:

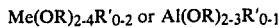

in which Me denotes Si or Ti, R is alkoxy having 1 to 5 C atoms and R' is a methyl or ethyl group.

17. The process of claim 13, wherein the product is dried.

18. The process of claim 13, wherein the product is milled and classified.

19. A process for preparing a polymeric ammonium compound with a silica-type backbone as claimed in claim 1, comprising reacting a secondary bis-(trialkoxysilylorgano)-amine with a halogenoorganotrialkoxysilane, the organic groups of which correspond to R⁵ in the formula (2) or with a linear or branched alkyl halide containing 1 to 20 C atoms, or with a cycloalkyl halide containing 5 to 8 C atoms or benzyl halide or with an inorganic or organic protonic acid and thereafter hydrolyzing and polycondensing the resulting quaternary salt by reacting it with stoichiometric or excess, relative to quantitative hydrolysis and condensation, amounts of water, and separating the product from the liquid phase.

20. The process of claim 19, wherein a solubilizer is present in the reaction.

21. The process of claim 20, wherein the solubilizer is an alcohol which corresponds to the particular alkoxy groups on the Si atoms.

22. The process of claim 19, wherein a crosslinking agent is present of the formula:

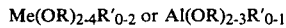

in which Me denotes Si or Ti, R is an alkoxy radical having 1 to 5 C atoms and R' is a methyl or ethyl group.

23. A processs for preparing a polymeric ammonium compound as claimed in claim 1, comprising quaternizing a secondary amine having substituents comprised of a trialkoxysilylorgano group and a linear or branched alkyl group containing 1 to 20 C atoms or a cycloalkyl group containing 5 to 8 C atoms or a benzyl group with a halogenoorganotrialkoxysilane in which the organic groups correspond to the group $R^5$ in claim 1 and thereafter hydrolyzing and polycondensing the resulting quaternary salt by reacting it with stoichiometric or excess, relative to quantitative hydrolysis and condensation, amounts of water, and separating from the liquid phase.

24. The process of claim 23, wherein a solubilizer is present in the rection.

25. The process of claim 24, wherein the solubilizer is an alcohol which corresponds to the particular alkoxy groups on the Si atoms.

26. The process of claim 23, wherein a crosslinking agent is added of the formula:

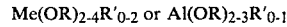

in which Me denotes Si or Ti, R is an alkoxy radical having 1 to 5 C atoms and R' is a methyl or ethyl group.

27. The process of claim 23, wherein the product is dried.

28. The process of claim 27, wherein the dried product is milled and classified.

29. A process for preparing a polymeric ammonium compound as claimed in claim 1, comprising quaternizing a tertiary tris-(trialkoxysilylorgano)-amine the organic groups of which correspond to the group $R^5$ in claim 1 and the alkoxy groups of which have 1 to 5 C atoms with a linear or branched alkyl halide containing 1 to 20 C atoms or with a cycloalkyl halide containing 5 to 8 C atoms, with a benzyl halide or with an inorganic or organic protonic acid or with a halogenoorganotrialkoxysilane the organic group of which corresponds to the group $R^5$ in claim 1 and thereafter hydrolyzing and polycondensing the resulting quaternary salt by reacting it with stoichiometric or excess, relative to quantitative hydrolysis and condensation, amounts of water and separating the product from the liquid phase.

30. The process of claim 23, wherein a solubilizer is present in the reaction.

31. The process of claim 30, wherein the solubilizer is an alcohol which corresponds to the particular alkoxy groups on the Si atoms.

32. The process of claim 29, wherein a crosslinking agent is present of the formula:

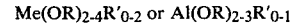

in which Me denotes Si or Ti, R is an alkoxy radical having 1 to 5 C atoms and R' is a methyl or ethyl group.

33. The process of claim 29, wherein the product is dried.

34. The process of claim 29, wherein the product is milled and classified.

35. A process for preparing a polymeric ammonium compound as claimed in claim 1, comprising quaternizing a tertiary amine, the substituents of which are comprised of 2 trialkoxysilylorgano radicals, the organic groups of which correspond to the group $R^5$ in claim 1 and of a linear or branched alkyl group containing 1 to 20 C atoms or of a cycloalkyl group containing 5 to 8 C atoms or of the benzyl group with a halogenoorganotrialkoxysilane, the organic group of which corresponds to the group $R^5$ in claim 1 or with a linear or branched alkyl halide containing 1 to 20 C atoms, a cycloalkyl halide containing 5 to 8 C atoms or with a benzyl halide or with an inorganic or organic protonic acid and thereafter hydrolyzing and polycondensing the resulting quaternary salt by reacting it with stoichiometric or excess, relative to quantitative hydrolysis and condensation, amounts of water, and separating the product from the liquid phase.

36. The process of claim 35, wherein a solubilizer is present in the reaction.

37. The process of claim 36, wherein the solubilizer is an alcohol which corresponds to the particular alkoxy groups on the Si atoms.

38. The process of claim 35, wherein a crosslinking agent is present of the formula:

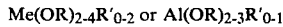

in which Me denotes Si or Ti, R is an alkoxy radical having 1 to 5 C atoms and R' is a methyl or ethyl group.

39. The process of claim 35, wherein the product is dried.

40. The process of claim 39, wherein the product is milled and classified.

41. A process for preparing a polymeric ammonium compound as claimed in claim 1, comprising quaternizing a tertiary amine, the substituents of which are comprised of 1 trialkoxysilylorgano radical the organic group of which corresponds to the group $R^5$ in claim 1 and of 2 further organic radicals which are identical or different to one another in the form of a linear or branched alkyl group containing 1 to 20 C atoms and/or of a cycloalkyl group containing 5 to 8 C atoms and/or of the benzyl group with a halogenoorganotrialkoxysilane, the organic group of which corresponds to the group $R^5$ in claim 1 and thereafter hydrolyzing and polycondensing the resulting quaternary salt by reacting it with stoichiometric or excess, relative to quantitative hydrolysis and condensation, amounts of water, and separating the product from the liquid phase.

42. The process of claim 41, wherein a solubilizer is present in the reaction.

43. The process of claim 42, wherein the solubilizer is an alcohol which corresponds to the particular alkoxy groups on the Si atoms.

44. The process of claim 41, wherein a crosslinking agent is present of the formula:

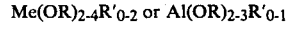

in which Me denotes Si or Ti, R is an alkoxy radical having 1 to 5 C atoms and R' is a methyl or ethyl group.

45. The process of claim 41, wherein the product is dried.

46. The process of claim 45, wherein the dried product is subjected to milling and classifying.

47. The process for preparing a polymeric ammonium compound, as claimed in claim 13, wherein the quaternization of the amine is carried out with the use of a solvent.

48. The process for preparing a polymeric ammonium compound, as claimed in claim 13, wherein the quaternization is carried out below, at or above room temperature up to a temperature of 300° C. under atmospheric pressure or an overpressure which corresponds to the sum of the partial pressures of the individual components of the reaction mixture.

49. The process for preparing a polymeric ammonium compound, as claimed in claim 13, wherein the hydrolysis and condensation of the quaternary salts is carried out at room temperature to the reflux temperature of the reaction mixture.

50. A process for preparing a polymeric ammonium compound as claimed in claim 1, and a particular polymeric ammonium compound in which $R^3$ and/or $R^4$ are not hydrogen and in which at the same time the anion is no halide, comprising reacting the quaternized, undried, dried and/or heat-treated polymeric ammonium compound which is completely substituted by organic and organosilyl groups with an inorganic or organic reagent which can dissociate into a cation and an anion for the purpose of mutual exchange of anions according to the static or dynamic ion exchange principle, thereafter washing the solid.

51. The process of claim 50, wherein the polymeric solid is separated from the liquid or gaseous phase.

52. The process of claim 50, wherein the product is dried.

53. The process of claim 52, wherein the product is milled, classified and heat-treated.

54. The process as claimed in claim 50, wherein the ion exchange is carried out in an agitated suspension of the polymeric starting ammonium compound with the at least partially dissolved reactant or the starting compound, as an ion exchange bed, is brought into contact with the solution of the reactant.

55. An ion exchange material comprising the polymeric ammonium compound as defined in claim 1.

56. The process of preparing a polymeric ammonium compound as claimed in claim 7, wherein drying is carried out at room temperature to 300° C.

57. The process of preparing a polymeric ammonium compound as claimed in claim 13, wherein drying is carried out at room temperature to 300° C.

58. The process of preparing a polymeric ammonium compound as claimed in claim 7, wherein heat treatment is carried out for at least one hour up to 4 days at 200°–400° C.

59. The process of preparing a polymeric ammonium compound as claimed in claim 13, wherein heat treatment is carried out for at least one hour up to 4 days at 200°–400° C.

* * * * *